(12) United States Patent
Grano et al.

(10) Patent No.: US 10,576,127 B2
(45) Date of Patent: Mar. 3, 2020

(54) IRISIN FOR CARE AND PREVENTION OF OSTEOPOROSIS

(71) Applicants: UNIVERSITA' DEGLI STUDI DI BARI, Bari (IT); UNIVERSITA' POLITECNICA DELLE MARCHE, Ancona (IT)

(72) Inventors: Maria Grano, Bari (IT); Graziana Colaianni, Bari (IT); Concetta Cuscito, Bari (IT); Giacomina Brunetti, Bari (IT); Silvia Colucci, Bari (IT); Saverio Cinti, Torrette di Ancona (IT); Giorgio Mori, Foggia (IT)

(73) Assignees: UNIVERSITA' DEGLI STUDI DI BARI, Bari (IT); UNIVERSITA' POLITECNICA DELLE MARCHE, Ancona (IT)

( * ) Notice: Subject to any disclaimer, the term of this patent is extended or adjusted under 35 U.S.C. 154(b) by 54 days.

(21) Appl. No.: 15/880,725

(22) Filed: Jan. 26, 2018

(65) Prior Publication Data

US 2018/0153960 A1    Jun. 7, 2018

Related U.S. Application Data

(62) Division of application No. 15/098,418, filed on Apr. 14, 2016, now abandoned.

(30) Foreign Application Priority Data

Apr. 16, 2015   (IT) .............................. MI2015A0558

(51) Int. Cl.
*A61K 38/17*    (2006.01)
*A61K 38/22*    (2006.01)

(52) U.S. Cl.
CPC .............. *A61K 38/17* (2013.01); *A61K 38/22* (2013.01)

(58) Field of Classification Search
None
See application file for complete search history.

(56) References Cited

U.S. PATENT DOCUMENTS

| | | | |
|---|---|---|---|
| 5,288,931 A * | 2/1994 | Chang ................. | C07K 1/1133 435/69.1 |
| 7,112,660 B1 * | 9/2006 | Domingues ........ | C07K 14/5406 424/85.2 |
| 2003/0045474 A1 * | 3/2003 | Sailer ................. | A61K 38/1875 514/8.8 |
| 2013/0074199 A1 | 3/2013 | Spiegelman | |
| 2014/0154743 A1 * | 6/2014 | Levy ................... | C07K 14/245 435/69.6 |

OTHER PUBLICATIONS

Tokuriki et al., 2009, Curr. Opin. Struc. Biol. 19:596-604).*
Bhattacharya et al. (2017, PLoS ONE 12(3): e0171355, https://doi.org/10.1371/journal.pone.0171355).*
Alaoui-Ismaili (2009, Cytokine Growth Factor Rev. 20(5-6):501-7).*
Guo et al. (2004, PNAS USA 101(25):9205-10).*
Ulloa-Aguirre et al. (2004, Traffic 5:821-837).*
Bernier et al. (2004, Curr. Opin. Pharmacol. 4:528-533).*
Graziano Colaianni et al:"Irisin Enhances Osteoblast Differentiation in Vitro", International Journal of Endocrinology, vol. 43, No. 8 Jan. 1, 2014, pp. 615-618.
Zhang Jin et al.: "Abstract 1222—Exercise Strenghtens Bone though Myokine Irisin" Journal of Bone and MIneral Reserach, Blackwell Science, Inc., US, vol. 27, No. Suppl. 1, Jan. 1, 2012.
Andrea Palermo et al.:"Irisin is associated with osteoporotic farctures independently of bone mineral density . . . " Clinical Endocrinology vol. 82, No. 4, Jan. 6, 2015 pp. 615-619.
Search Report dated Dec. 4, 2015 for Italian Patent Application No. IT-MI2015A000558.
European Search Report dated Jun. 30, 2016 for European Patent Application No. EP16165324.1.

* cited by examiner

*Primary Examiner* — Elizabeth C. Kemmerer
(74) *Attorney, Agent, or Firm* — Silvia Salvadori

(57) ABSTRACT

An object of the present invention is the use of Irisin for the treatment and/or prevention of osteoporosis. In particular, the present invention refers to the use of recombinant irisin for the treatment and/or prevention of osteoporosis. A method for preventing and/or treating osteoporosis by administering an effective amount of irisin to a subject, is provided.

7 Claims, 9 Drawing Sheets

Figure 1:
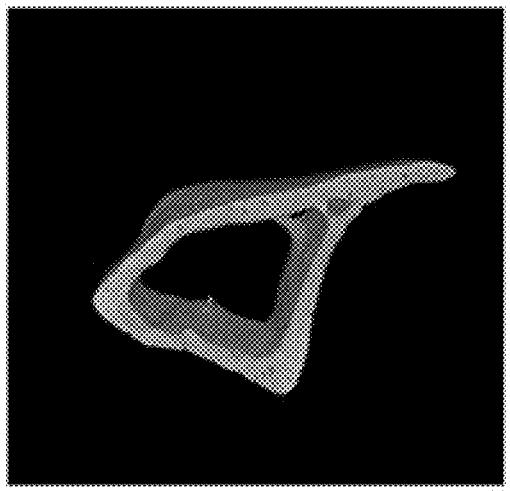
Figure 1:
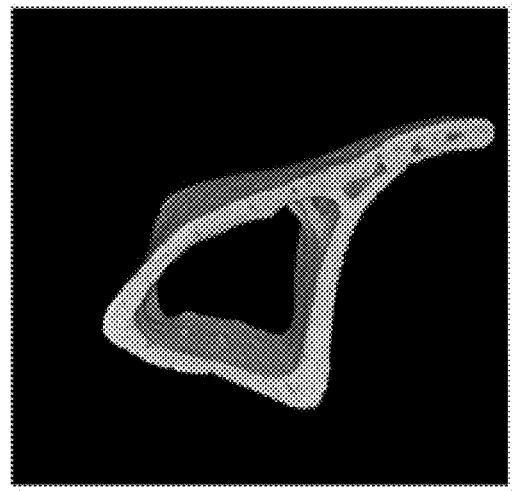
Figure 1:
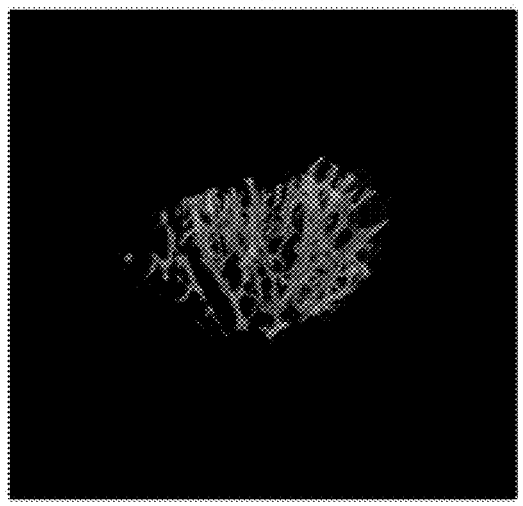
Figure 1:
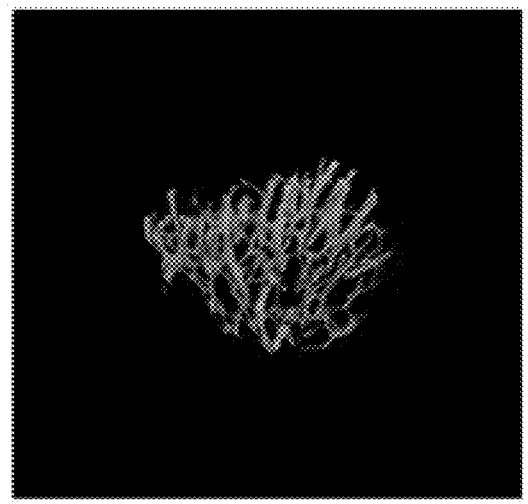

Specification includes a Sequence Listing.

Healthy murine model: young mouse cortical bone a
placebo-inj | irisina-inj trabecular bone b
placebo-inj | irisina-inj Osteoporotic murine model: elderly mouse Osteoporotic murine model: elderly suspended mouse cortical bone trabecular bone

IRISIN FOR CARE AND PREVENTION OF OSTEOPOROSIS

RELATED APPLICATIONS

This application is a divisional application of pending U.S. application Ser. No. 15/098,418 filed Apr. 14, 2016, now abandoned, which claims priority to Italian national application No. MI2015A000558, filed 16 Apr. 2015, the contents of each of which are hereby incorporated by reference as if set forth in their entireties.

SUMMARY

An object of the present invention is the use of Irisin for the treatment and/or prevention of osteoporosis.

TECHNICAL BACKGROUND

In the last ten years, the overall incidence of osteoporosis and fractures related to bone fragility increased by about 30%. Such an increase is partly linked to the higher life expectancy of the population in the last 50 years. In general, osteoporosis is a global health problem: the World Health Organization considers osteoporosis as the second critical health problem, preceded only by cardiovascular diseases. Based on the estimates made by the World Health Organization, in 2050 about 6.3 million of femoral fractures can occur, about 4.6 million more than in 1990. In Italy, femoral fractures caused by osteoporosis cost to the health service (SSN) 6.8 billion euros every 5 years. Considering that femoral fractures increase within each decade both for women (28%) and men (36%), it follows an increased need of hospital stays or home care, with remarkable increase of costs to be paid by the SSN. In Italy, it is estimated that each year from 70,000 to 90,000 hospitalizations for femoral fracture occur and it is estimated that the health expenditure for direct costs amounts to 568 million Euro per year. Therefore, the use of a drug/supplement targeting the reduction of the risk of fracture, would allow a remarkable reduction of expenditure by the SSN with remarkable economic benefits, in addition to improving the quality of life of the elderly population.

Osteoporosis is a condition wherein the skeleton is subjected to a loss of bone mass and resistance, due to multiple factors such as, for example, nutritional, metabolic or pathologic factors. Thus, the skeleton is subjected to higher risk of fractures, following to the decrease in bone density and changes and/or alterations occurring at the level of the microarchitecture of the bones.

Generally, osteoporosis predisposes, as mentioned, to greater development of fractures, both traumatic and pathologic, consequently leading to a reduction in the life quality and expectancy. Furthermore, it must not be overlooked the aspect caused by the possibility of the occurrence of complications due to the fractures, if not properly treated.

A number of therapies for osteoporosis are known. For example, the supplementation of D3 vitamin is helpful both in healthy subjects to carry out preventive action, and in osteoporotic and osteopenic subjects. The two forms of D vitamin used are D2 vitamin (ergocalciferol) and D3 vitamin (cholecalciferol), orally or intramuscularly administrable.

Other known supplementary treatments, which produce a beneficial effect at the bone level, are for example the supplementation of calcium (for example calcium carbonate), magnesium (for example in the form of magnesium pidolate) and various other microelements, such as manganese, boron, strontium, silicon and zinc.

In the care of osteoporosis so called "antiresorptive" drugs, that is drugs acting by reducing or blocking the bone erosion mediated by osteoclasts and with this mechanism being able to considerably reduce pathologic fractures, are also used. Some examples of these drugs are: denosumab, alendronate, risedronate, ibandronate, neridronate, clodronate, zoledronate, calcitonin, and drugs acting on hormonal levels such as raloxifene, bazedoxifene, lasofoxifene, tibolone, TOS with estrogen-progestin, testosterone (androgens).

Another example of used drug is strontium ranelate (a strontium salt), which is the initiator of a class of drugs known as DABA (Dual Action Bone Agents), the characteristic of which is to have a dual action. In fact, strontium ranelate acts both as an antiresorptive drug and as an anabolic drug. In other words, strontium ranelate acts both by suppressing osteoclasts and, at the same time, stimulating the production and activity of the osteoblasts, thereby inducing an increase of bone mineral density (BMD).

Also drugs known as "osteoforming", characterized by an action mechanism based on the bone reconstruction, as opposed to the so called "antiresorptive" drugs, that are limited instead to reduce the bone erosion, are used.

OBJECTS OF THE INVENTION

Thus, object of the present invention is to provide a compound that may be used in the treatment and/or prevention of osteoporosis.

Another object of the present invention is to provide a compound that may be used in the treatment and/or prevention of osteoporosis as a substitute for physical exercise.

Also, an object of the present invention is to provide a compound not having side effects and that may be used individually or in combination with other therapies.

Still another object of the present invention is to provide a compound that may be used as a supplement, for the prevention of osteoporosis.

DETAILED DESCRIPTION

The above-mentioned objects and still other objects that will be better clarified hereinafter, are achieved by the present invention, whose object is irisin used in the treatment of osteoporosis.

In fact, it has surprisingly been verified that irisin exerts a direct anabolic action on the bone tissue. Irisin is known for its ability to induce trans-differentiation of the white adipocytes into brown. Surprisingly, it has been observed that it is also able to exert a direct action on cells of the bone tissue, such as osteoblasts and precursors thereof.

Irisin is a protein. In humans, irisin is codified by the FNDC5 gene. More precisely, the FNDC5 gene codifies a pro-hormone known as "Fibronectin type III domain-containing protein 5" that, following to proteolytic cleavage occurring at the level of plasma membrane, gives rise to irisin.

The first role described for the irisin molecule is to induce trans-differentiation of white adipose tissue into brown. Irisin activates the so-called "browning" phenomenon, i.e. it acts on the adipocytes present in the deposits of white adipose tissue by inducing their trans-differentiation into brown adipocytes, whose main function is to regulate the thermogenesis. Therefore, such a molecule is currently a candidate to cure obesity.

It has been demonstrated that the therapeutic treatment with irisin of normal and obese mice induced a potent trans-differentiation of the white adipocytes into brown adipocytes. The effect was dependent by the expression increase of a marker of brown adipocyte, UCP1 (uncoupling protein 1), in mice treated with irisin and went with a significant reduction of body weight in these mice.

Other studies revealed that cerebellar Purkinje cells of rat and mouse express irisin, whose function would be to induce the neuronal differentiation of embryonic stem cells of mouse.

It is also known that the energetic depletion, peculiar to myocardial infarction, negatively affects the circulating concentration of irisin, indicating a negative association of this myokine with infarction. In fact, it has been demonstrated that its synthesis is reduced in the 4 hours following to the ischemic event and it is suggested that irisin may be named among the novel markers of infarction.

Other known uses are, for example, the use of irisin in inducing the oxidation of fatty acids and mitochondrial biogenesis, as well as its use to prevent the damage by post-ischemic reperfusion after infarction.

Object of the present invention is an innovative and advantageous use of irisin, i.e. irisin is used in the treatment and/or prevention of osteoporosis.

In fact, it has been observed that irisin exerts an anabolic action on the bone tissue, i.e. it induces an increase of the osteoblastic differentiation starting from precursors present in the bone marrow as well as an increase of the type I collagen, the most abundant protein of the bone matrix, production.

The present invention is particularly advantageous because irisin can be used in the treatment of different osteoporotic conditions, characterized by loss of bone mass such as, for example, osteoporosis in aging, immobility osteoporosis, muscular degeneration (sarcopenia), cachexia associated with tumor, neuromuscular diseases, osteoporosis due to the absence of mechanical loading (microgravity, such as for example in the case of absence of gravity to which the astronauts are subjected in the long periods of time spent in space during space missions), as well as for the cases of post-menopausal osteoporosis. Furthermore, it has surprisingly been observed, according to the present invention, that irisin can play an exercise-mimetic effect; in other words, it has been observed that its administration produces the same beneficial effects of a regular physical exercise. By virtue of this surprising exercise-mimetic effect, according to the present invention, irisin can be used with therapeutic and/or prevention aims instead of the physical exercise. For example, it can be advantageously used in subjects having the above-mentioned conditions, which are in such a condition not able to practice physical exercise, such as for example particularly debilitated elderly persons, or persons having motor disabilities or paralyses. According to the present invention, in addition to the already discussed advantages, irisin can be used as supplement, also with preventive purpose. By way of example, irisin can be administered with preventive purpose in healthy subjects also of young age, in particular if at risk of osteoporosis, which are practicing little or no physical exercise.

In the treatment of osteoporosis, according to the present invention irisin can be administered, in conveniently calibrated doses, alone or in conjunction with other drugs, preferably drugs already known for the treatment of osteoporosis.

It is another object of the present invention a composition comprising irisin used for the treatment and/or prevention of osteoporosis. According to a preferred embodiment, such compositions can comprise excipients and/or additives for pharmaceutical use.

According to an embodiment, irisin according to the invention is recombinant irisin.

According to the present invention, by the term "recombinant irisin" is meant irisin obtained by transcription and translation of a coding DNA fragment, precisely irisin, in a host organism normally not expressing it. Still according to the invention, as a host organism for example bacteria can be used, from which the protein, i.e. recombinant irisin, is subsequently extracted and purified.

In a preferred embodiment, such a recombinant irisin comprises the following amino acid sequence:

(SEQ. ID NO. 1)
DSPSAPVNVTVRHLKANSAVVSWDVLEDEVVIGFAISQQKKDVRMLRFI

QEVNTTTRSCALWDLEEDTEYIVHVQAISIQGQSPASEPVLFKTPREAEK

MASKNKDEVTMKE

Preferably, recombinant irisin according to the present invention is constituted by the amino acid sequence SEQ. ID NO. 1.

According to another embodiment, the amino acid sequence of irisin for use in the treatment and prevention of osteoporosis according to the present invention, shows a percentage of sequence identity to SEQ. ID NO. 1 between 60% and 99%, preferably between 80% and 99%, more preferably between 90% and 99%, and even more preferably between 95% and 99%.

According to the present invention, by "identity percentage" is meant the degree of matching between the reference sequence and possible other sequences according to the invention.

According to another embodiment of the present invention irisin, preferably recombinant irisin, is administered at a dosage between 500 µg/kg and 50 µg/kg, preferably between 250 µg/kg and 75 µg/kg. According to another preferred embodiment of the present invention irisin, preferably recombinant irisin, is administered at a dosage of 100 µg/kg.

The µg/kg unit of measure denotes that the dosage of irisin is calibrated to the body weight of the subject or animal to which such a molecule will be administered; particularly, it is defined as the amount of irisin (by weight, expressed in µg) to be administered per each kg of the patient or animal model.

The present invention, the object of which is irisin used in the treatment of osteoporosis, shows a further advantage. The irisin, according to the invention, is used with surprising results in the treatment of osteoporosis, also in the absence of physical exercise needed instead as a support of the action of the treatments know to date. In fact, all the therapies for the prevention and/or treatment of osteoporosis currently known are based, for their optimal success, on the association between pharmacological drug therapy and supporting physical exercise. This aspect can represent an also remarkable problem in the case of subjects unable (by the age, temporary or permanent general conditions, etc.) to practice even mild physical exercise.

The benefits of physical exercise are widely recognized, so that physical exercise is considered among the best non-drug treatments supporting drug treatments themselves, for important conditions such as diabetes, cardiovascular diseases, obesity and, precisely, osteoporosis. In fact, it is believed that many of the factors involved in the osteoporosis onset, such as for example hormonal changes, absence of physical exercise, low protein intake in the diet and the chronic inflammation, contribute to the concomitant onset of sarcopenia and osteoporosis. For example, a child growing up with congenital neuromuscular diseases, develops long and fragile bones with a reduced periosteal circumference. The paralytic phenotype of children affected by spina bifida is characterized by a mineralization delay of the bone matrix in long bones of the paralyzed limb.

According to the present invention, it has been surprisingly observed that the irisin treatment not only reduces and/or prevents the degeneration of the bone mass and thus the osteoporosis onset, but it is also able to mimic the combined effect of the drug treatment associated with a significant physical exercise.

Object of the invention, according to another of its aspects, is a method of preventing and/or treating osteoporosis, comprising administering an effective amount of irisin to a subject in the need thereof.

The above indicated preferred embodiments of the invention are also applied to the treatment method of the invention.

As it will then be defined in more detail within the experimental section, the effectiveness of irisin in the treatment and/or prevention of osteoporosis has been observed by a study performed in vivo, by using experimental murine models of healthy and osteoporotic mice administered with irisin for 4 weeks. At the end of the treatment, some skeletal segments of the animals have been subjected to skeleton analysis by computerized micrography (microCT).

In a first group of animals of 3 months old C57BL6 mice (group 1, young and healthy mouse), it has been observed that tibias of mice treated with irisin showed an increase of cortical bone mineral density (BMD) of about 10% compared to that of mice maintained in the same conditions and injected with placebo. Furthermore, it has been possible to hypothesize that the administration of irisin would modify the cortical bone geometry, because it has been observed an increase of the periosteal circumference and polar moment of inertia (pMOI). The latter two parameters are respectively indicative of resistance of long bones against bending and torsion. In other groups of animals, i.e. in murine models of osteoporosis which formed further groups of animals (2, 3, 4 and 5), the surprising effectiveness of irisin in the treatment of osteoporosis found further confirmation. In murine models of osteoporosis, which formed further groups of employed animals (2, 3, 4 and 5), the condition of osteoporosis has been accomplished by using the suspended young mouse, the elderly mouse, the suspended elderly mouse and the young ovariectomized mice. Specifically, the "suspended" murine model is that one widely used and accepted in the scientific community in order to evaluate the loss of bone mass depending on the absence of mechanical loading (condition which, for example, immobilized persons and astronauts during space missions are subjected to). In particular, according to the present invention, the so called "suspended" mouse model provides for the rodent being suspended by the tail, so that the hind limbs are off the ground and are not no more subjected to mechanical loading. In such animals the ambulation is only allowed by the forelimbs.

The suspension of rodents by the tail is a consolidated approach in order to create, on the earth, a model of microgravity and/or musculoskeletal disuse simulating the physiological changes associated with space flight, or those occurring during immobilization in bed for long periods.

The treatment with recombinant irisin in elderly mice allowed to confirm the effect of irisin on the bone tissue degenerated following the ageing.

In the second group of animals of 3 months old C57BL6 mice (group 2, young osteoporotic murine model: "suspended" mouse), the results obtained by the microCT analysis demonstrated that young mice maintained for 4 weeks in the absence of mechanical loading, lost 5% of cortical bone mineral density (BMD) compared to the mice maintained in control conditions (normal ambulation). On the contrary, in mice suspended and at the same time treated with irisin, the BMD reduction was surprisingly completely zeroed. Also at the level of the trabecular component of tibia, where a BMD reduction by 39% was found in the suspended mouse compared to one normally able to ambulate, it has been observed that the irisin treatment minimized the loss to 23%, thus with an improvement by 16% of the bone mineral density to the controls. Furthermore, in suspended mice a reduction of bone volume to total volume ratio (BV/TV) by 47% has been observed, whereas in the suspended ones and at the same time treated with irisin, such a reduction is lessened by 6%. This lessening can be explained by an increase of the number of bone trabeculae. In fact, it has been observed that, whereas the mice suspended and treated with placebo showed 65% less in trabecular number compared to the controls, the mice suspended and injected with irisin only showed 52% less trabeculae, thus showing a loss reduction of trabecular number by 13%. Such a figure takes on a great importance if we are considering that the integrity of the trabecular bone is fundamental for the resistance of cortical bone against fractures and further represents the component subjected to higher deterioration in all forms of osteoporosis.

Thus, such results confirmed that irisin can effectively be used in the treatment of osteoporosis, for example in osteoporosis due to the absence of mechanical loading (microgravity).

The effectiveness of irisin in senile osteoporosis has been confirmed by using elderly mice. Senile osteoporosis is characterized by a gradual reduction of bone mass, caused by the metabolic condition generating from the reduction of the estrogen levels and which is also dramatically worsened due to the reduced ambulation and muscular degeneration. In fact it is well documented that, in elderly subjects both men and women, bioavailable circulating estradiol (known as 17β-estradiol or E2) declines down to the concentration of 11 pg/ml and, below this threshold, the loss rate of bone mass becomes inversely proportional to its concentration. It's important to highlight that estrogens are able to bind the androgen receptor and, above all, that androgens can be converted in estrogens. The conversion of androgens to estrogens occurs through a process involving the aromatase enzyme, which is widely distributed and highly conserved among the vertebrates. This enzyme converts androstenedione, testosterone and 16α-hydroxytestosterone in estrone, estradiol and estriol, respectively.

In the third group of animals of 15 months old C57BL6 mice (group 3, osteoporotic murine model: elderly mouse), characterized by an important loss of bone mass involving both the cortical and trabecular components, the effectiveness of irisin in the treatment of senile osteoporosis has been confirmed. In fact, in mice treated with irisin, an increase of cortical bone mineral density by about 8% and an increase of the trabecular one by 24% compared to the placebo, have been observed. Furthermore in elderly mice, in which the trabecular bone mass (BV/TV) of tibia is on average lower by 55% compared to that of a 3 months old young mouse, the irisin treatment has been effective in the stimulation of the recovery of bone mass: in fact, a recovery of bone mass of 12%, related to an increase of the trabecular number, has been observed.

The fourth group of animals of 15 months old C57BL6 mice (group 4, osteoporotic murine model: elderly "suspended" mouse), representing a murine model of osteoporosis in aging along with immobility, confirmed the effects of irisin on the recovery of bone mass in those pathological conditions wherein a reduced or absent ambulation is also associated with the drop of the level of steroid hormones, such as for example in elderly bedridden patients.

The microCT results demonstrated that in the tibias of elderly suspended mice, wherein normally the loss of cortical BMD is worsened by 10% compared to the mice freely ambulating, the irisin treatment reduces such a loss to 5%. Regarding the mineral density of the trabecular bone, in elderly suspended mice being reduced by about 45% compared to that of the elderly ambulating mice, the irisin treatment reduces such a loss by 15%, in fact in such animals a reduction of bone mineral density by 30% only has been observed. The drastic reduction of bone mass, observed in elderly suspended mouse, is also confirmed by the alterations of the other parameters of the trabecular bone. The reduction of trabecular mass, characterizing the elderly suspended mouse compared to the elderly mouse that can normally ambulate, confirms the worsening of the bone fragility appearing when the immobilization is also associated with the osteoporosis in aging caused by the decline of sex hormones and other metabolic alterations. In fact, BV/TV (bone volume to total volume ratio) at the level of trabeculae of the tibias, in elderly suspended mice is reduced by 70% compared to the controls; it has been observed that the irisin treatment reduces such a loss by 20%, in fact in the treated animals a BV/TV reduction by 50% has been observed. Furthermore, it has been observed that the trabecular number, in the elderly suspended mouse, is reduced by ⅓ and that the irisin treatment reduces such a loss by 20%.

The fifth group of animals of 6 weeks old C57BL6 ovariectomized mice (group 5: post-menopausal osteoporosis murine model), representing a murine model of menopausal osteoporosis, confirmed the effectiveness of irisin also in this type of osteoporosis.

In these mice a BV/TV reduction by 28% compared to the controls has been observed. It has been observed that the irisin treatment in ovariectomized mice induces the complete recovery of the loss of bone mass.

The experiments carried out in murine models described above have confirmed the surprising effectiveness of irisin in the treatment of osteoporosis; in particular, it has been possible to confirm that irisin can effectively be used in the treatment of osteoporosis, whether this being due to one or more factors such as, for example, senility, immobility, microgravity or menopause.

The following experimental evidence is reported as further support of the present invention.

The experimental results are together with the attached Figures.

FIG. 1 shows the 3D reconstruction of scans performed by microCT of tibias of mice belonging to the Group 1 of animals, that is the murine model of young and healthy mouse. Scans have been performed by Skyscan 1172, camera 11 MPix. Structural parameters have been calculated by using the Skyscan CT Analyzer software. For the properties of the cortical bone (Panel "a"), tibias of mice have been scanned in mid-diaphysis, at a distance of 5.5 mm from the proximal tibial condyles. For the properties of the trabecular bone (Panel "b"), tibias of mice have been scanned at a distance of 1.9 mm from the proximal tibial condyles, in a distal position to the epiphyseal plate, in the direction of the metaphysis. The reconstructions of samples deriving from mice treated with placebo (placebo-inj) and treated with irisin (irisin-inj) are showed.

Figure 2:
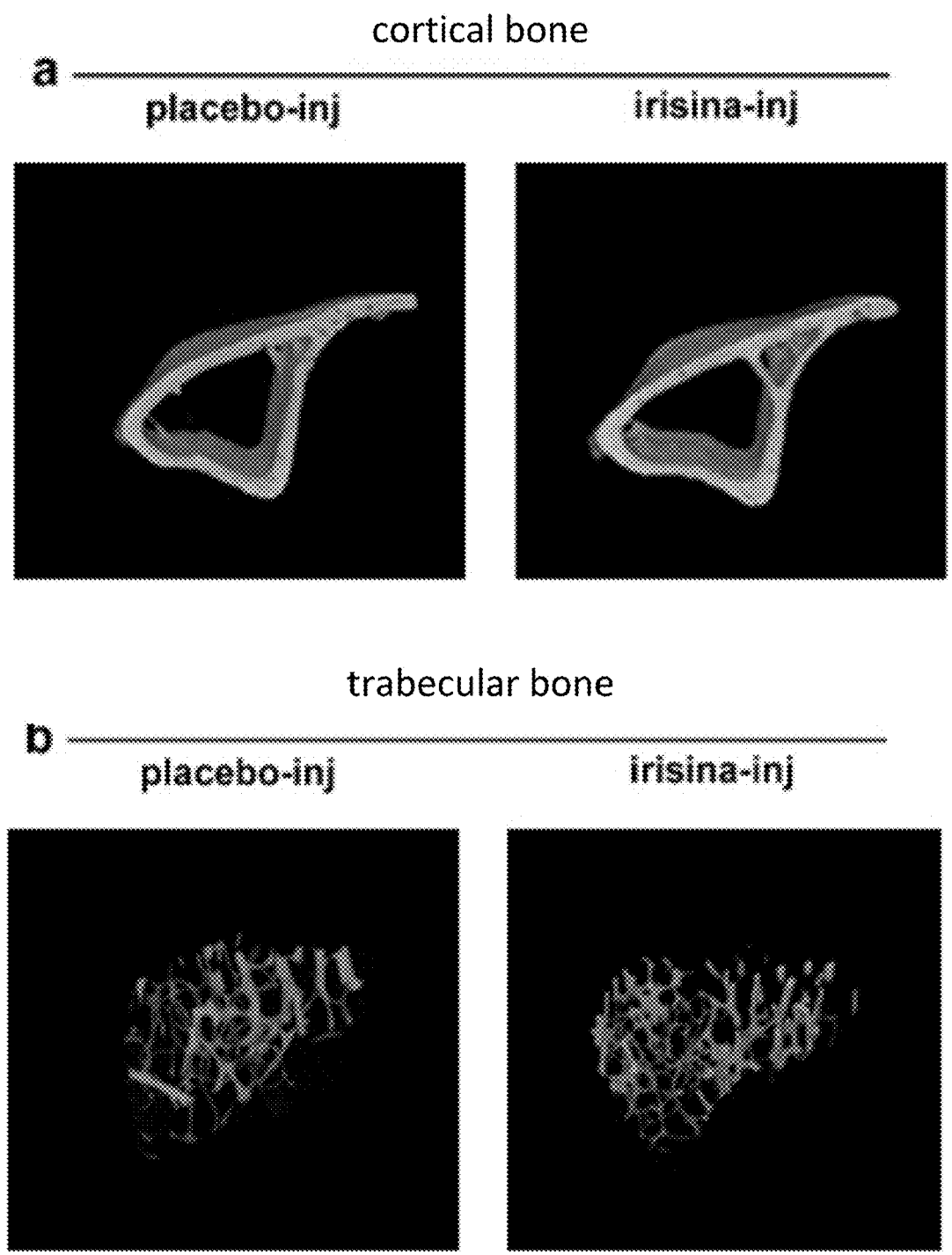

FIG. 2 shows the 3D reconstruction of scans performed by microCT of tibias of mice belonging to Group 2 of animals, that is the murine model of young osteoporotic "suspended" mouse. Scans have been performed as described for FIG. 1. Panel "a" shows reconstructions of cortical bone, whereas Panel "b" shows reconstructions of trabecular bone. The reconstructions of samples deriving from mice treated with placebo (placebo-inj) and treated with irisin (irisin-inj) are showed.

Figure 3:
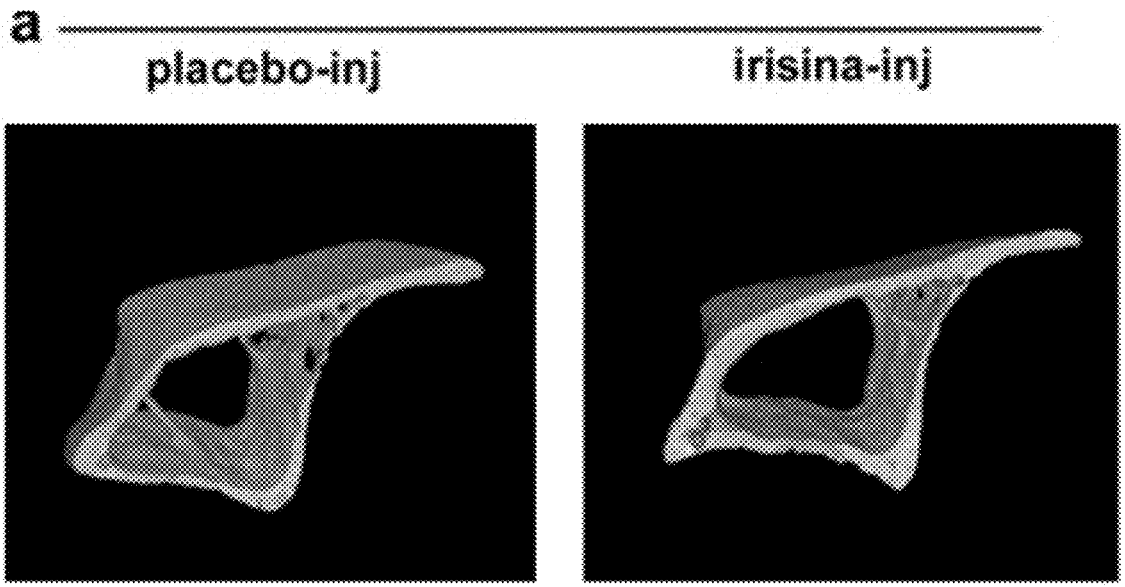
Figure 3:
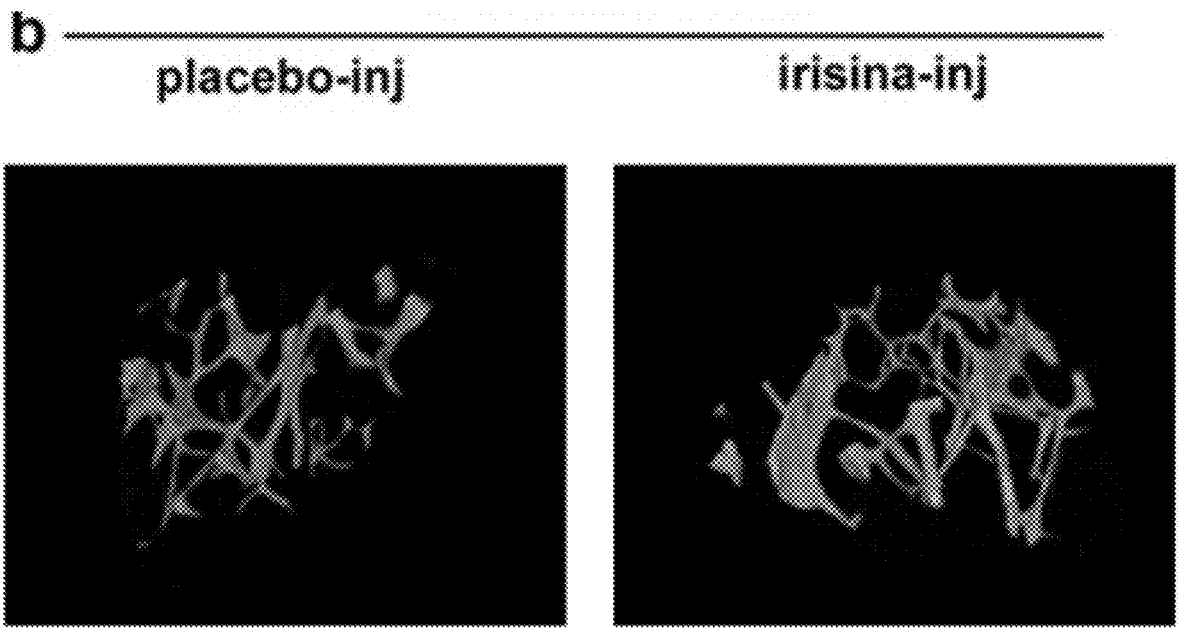

FIG. 3 shows the 3D reconstruction of scans performed by microCT of tibias of mice belonging to Group 3 of animals, that is the murine model of elderly osteoporotic mouse. Scans have been performed as described for FIG. 1. Panel "a" shows reconstructions of cortical bone, whereas Panel "b" shows reconstructions of trabecular bone. The reconstructions of samples deriving from mice treated with placebo (placebo-inj) and treated with irisin (irisin-inj) are showed.

Figure 4:
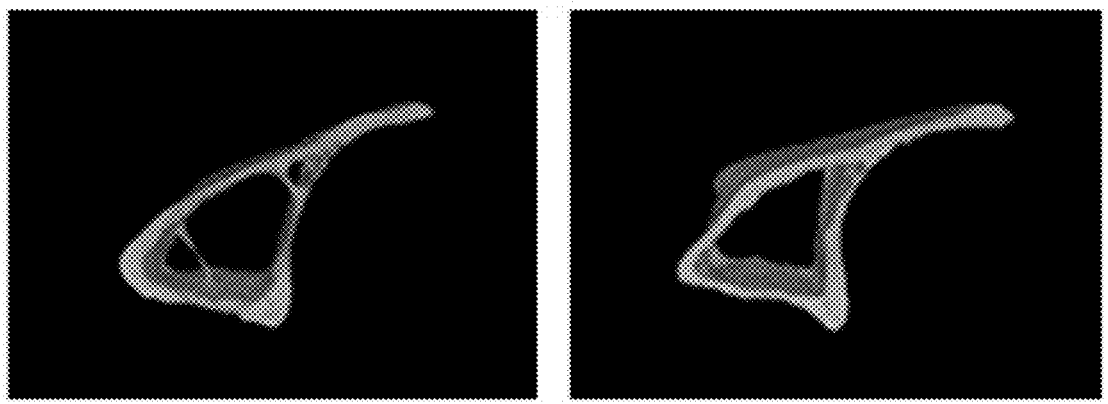
Figure 4:
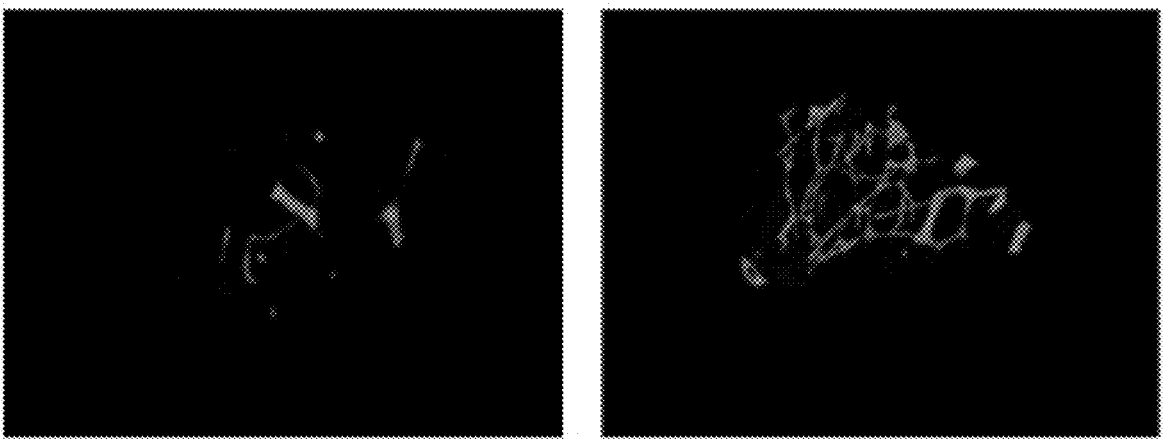

FIG. 4 shows the 3D reconstruction of scans performed by microCT of tibias of mice belonging to Group 4 of animals, that is the murine model of elderly osteoporotic "suspended" mouse. Scans have been performed as described for FIG. 1. Panel "a" shows reconstructions of cortical bone, whereas Panel "b" shows reconstructions of trabecular bone. The reconstructions of samples deriving from mice treated with placebo (placebo-inj) and treated with irisin (irisin-inj) are showed.

Figure 5:
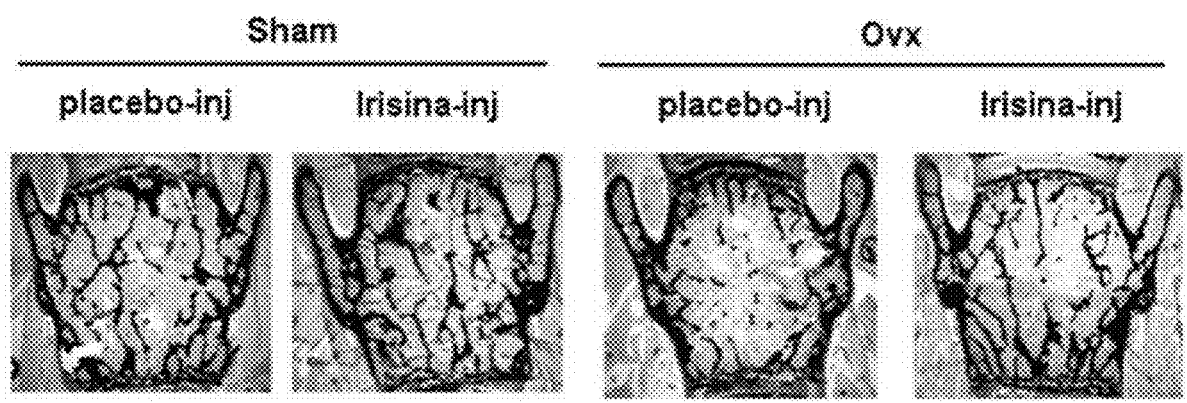

FIG. 5, shows sections (10 mm thickness) of lumbar vertebrae L3 and L4 of mice belonging to Group 5 of animals, that is the post-menopausal osteoporosis murine model: young ovariectomized mice. Such sections have been included in methyl-methacrylate and marked by Von Kossa/Van Gieson staining. Mice (n=3 per group) subjected to bilateral ovariectomy (Ovx) or surgery without removal of the ovaries (Sham), injected with placebo (placebo-inj) or Irisin 100 µg/kg (Irisin-inj).

FIGS. 6A, 6B, 6C and 6D show the results of experiments carried out to evaluate the biological effect and cellular mechanisms of irisin on murine osteoblasts in vitro.

EXPERIMENTAL SECTION

The anabolic action of irisin on the skeleton has been confirmed and demonstrated, after administering intraperitoneally 100 µg/kg recombinant irisin in C57BL6 mice, through analysis by computerized micrography (micro CT) and study of the differentiating parameters of the bone forming cells. This allowed demonstrating that the action of irisin on the bone is mediated by a direct effect of the molecule on the osteoblasts, that are the cells forming the new bone matrix. The choice of the administered dose has been made so that, in the 24 hours following the administration, the irisin reaches circulating levels of serum similar to those the molecule reaches in the animals subjected to physical exercise.

The experimental activity that allowed demonstrating the effect of irisin on the bone has been carried out on different groups of animals: group 1, healthy animals for the study of the basal effect of irisin; group 2, 3, 4 and 5 osteoporotic animals for the study of irisin on the care and prevention of the disease.

Group 1, Healthy Murine Model: Young and Healthy Mouse.

8 weeks old healthy C57BL6 mice have been intraperitoneally injected with 100 μg/kg/week recombinant irisin for 4 weeks. At the end of the treatment, by microCT analysis, tibias of mice treated with irisin (Irisin-inj) showed an increase of the cortical bone mineral density (BMD) by about 10% compared to those of mice maintained in the same conditions and injected with placebo (placebo-inj). Furthermore, it has also been demonstrated that administrating irisin modifies the cortical bone geometry; this has been possible through the analysis of two parameters that are index of resistance of long bones against bending and torsion, respectively. In particular, such parameters are the periosteal circumference (according to English terminology, "Bone Perimeter"), that increases by 7.25% compared to the placebo, and the polar moment of inertia (pMOI), that increases by 19.2% compared to the placebo. On the contrary, it hasn't been found any variation relative to the parameters of the trabecular bone. Results are described in detail in Table 1a (cortical bone) and in Table 1b (trabecular bone) and depicted in FIG. 1, Panels "a" and "b".

In the tables discussed in the present experimental section, the values of different parameters are reported; to identify such parameters the following acronyms and/or definitions have been used: BMD (bone mineral density), bone surface, periosteal circumference (Bone Perimeter), pMOI (polar moment of inertia) BV/TV, Bone Volume/Total Volume (bone volume to total volume ratio); trabecular number (Tb.N.); trabecular thickness (Tb.Th.); trabecular separation (Tb.Sep.). All the values are expressed as mean±standard error of the mean (SEM). In Tables 1a, 1b, 2a, 2b, 3a, 3b, 4a and 4b reported in the present experimental section, the asterisk and underlining are used to highlight the results where the P value (according to English terminology) is lower than 0.05, i.e. the data defined as statistically "significant".

TABLE 1a

Young and healthy mouse - Cortical bone of tibia

| Young healthy mouse | placebo-inj | Irisin-inj | P value |
|---|---|---|---|
| BMD (gr HA/cm$^3$) | 1.009 ± 0.02 | 1.081 ± 0.01* | 0.01 |
| Bone surface (mm$^2$) | 14.131 ± 0.26 | 15.195 ± 0.25* | 0.02 |
| Periosteal circumference (mm) | 12.014 ± 0.23 | 12.884 ± 0.24* | 0.03 |
| pMOI (mm$^4$) | 0.418 ± 0.02 | 0.499 ± 0.01* | 0.007 |

TABLE 1b

Young and healthy mouse - Trabecular bone of tibia

| Young healthy mouse | placebo-inj | Irisin-inj | P value |
|---|---|---|---|
| BMD (gr HA/cm$^3$) | 0.124 ± 0.01 | 0.133 ± 0.01 | 0.37 |
| BV/TV (%) | 5.113 ± 0.23 | 4.432 ± 0.26 | 0.07 |
| Trabecular thickness (μm) | 31.713 ± 0.80 | 32.210 ± 1.60 | 0.77 |
| Trabecular number (1/μm) | 0.0016 ± 0.0001 | 0.0014 ± 0.0001 | 0.08 |
| Trabecular separation (μm) | 218.96 ± 7.11 | 235.54 ± 11.4 | 0.23 |

Group 2, Osteoporotic Murine Model: Young "Suspended" Mouse.

8 weeks old C57BL6 mice have been subjected to the absence of mechanical loading, by suspension of the hind limbs, and treatment by intraperitoneal injection with 100 μg/kg/week recombinant irisin for 4 weeks. At the end of the treatment, by microCT analysis, tibias of non-treated mice (treated with placebo, placebo-inj) showed a reduction by 5% of cortical bone mineral density (BMD) compared to the mice maintained in conditions of normal ambulation and used as control. Data relative to controls, i.e. to mice maintained in conditions of normal ambulation, are the previously described data relative to Group 1.

Conversely, the suspended mice treated with irisin (Irisin-inj) didn't show loss of BMD compared to the control mice, thus demonstrating that the loss by 5% of BMD of suspended mice treated with placebo was completely recovered by administration of irisin.

From the analysis of the trabecular component of the tibias, in the suspended mouse a BMD reduction by 39% arose compared to that which could normally ambulate and a BMD reduction by 23% in mice suspended and treated with irisin. Therefore, it has been observed that the irisin treatment led to a reduction of BMD loss by 16% compared to the suspended mice treated with placebo. Furthermore, in suspended mice a reduction of bone volume to total volume ratio (BV/TV) by 47% has been observed, whereas in the suspended ones and at the same time treated with irisin such a reduction was by 42%, thus such loss was lessened by 5%. This reduction of loss can be associated to an increase of the trabecular number. In fact, in suspended mice a reduction of trabecular number by 65% has been observed, whereas in the suspended ones and at the same time treated with irisin such a reduction was by 52%. Therefore, it has been observed that the irisin treatment caused a reduction of loss of the trabecular number by 13%.

Results are described in detail in Table 2a (cortical bone) and in Table 2b (trabecular bone) and depicted in FIG. 2, Panels "a" and "b".

TABLE 2a

Young suspended mouse - Cortical bone of tibia

| Young suspended mouse | placebo-inj | Irisin-inj | P value |
|---|---|---|---|
| BMD (gr HA/cm$^3$) | 0.963 ± 0.01 | 1.02 ± 0.001* | 0.03 |
| Bone surface (mm$^2$) | 13.072 ± 0.07 | 13.902 ± 0.17* | 0.04 |
| Periosteal circumference (mm) | 11.296 ± 0.01 | 11.941 ± 0.10* | 0.02 |
| pMOI (mm$^4$) | 0.318 ± 0.01 | 0.387 ± 0.03* | 0.05 |

TABLE 2b

Young suspended mouse - Trabecular bone of tibia

| Young suspended mouse | placebo-inj | Irisin-inj | P value |
|---|---|---|---|
| BMD (gr HA/cm$^3$) | 0.076 ± 0.007 | 0.096 ± 0.01* | 0.02 |
| BV/TV (%) | 2.723 ± 0.84 | 3.009 ± 0.41* | 0.01 |
| Trabecular thickness (μm) | 46.32 ± 5.73 | 37.93 ± 1.89 | 0.2 |
| Trabecular number (1/μm) | 0.00057 ± 0.0001 | 0.00079 ± 0.0001* | 0.03 |
| Trabecular separation (μm) | 337.42 ± 7.02 | 284.83 ± 1.39* | 0.05 |

Group 3, Osteoporotic Murine Model: Elderly Mouse.

Elderly 15 months old C57BL6 mice have been treated by intraperitoneal injection with 100 μg/kg/week recombinant irisin for 4 weeks. Considering the present murine model, it should be noted that mice of this age show severe bone fragility caused by a reduction of bone mass both at cortical and trabecular level. At the end of the treatment, tibias of mice treated with irisin (irisin-inj) showed an increase of cortical BMD by about 8% and an increase of trabecular BMD by 24% compared to the elderly mice injected with placebo (placebo-inj). Furthermore, in elderly mice, in which the trabecular bone mass (BV/TV) of tibia is on average lower by 55% compared to that of a 3 months old young mouse, the irisin treatment causes a reduction of loss of bone mass by 12%. This recovery of bone mass is dependent upon an increase of the trabecular number. In fact, in an elderly mouse normally showing on average a trabecular number equal to ⅓ to a young healthy mouse, the irisin treatment caused a reduction of loss of the trabecular number by 7% compared to the elderly mouse injected with placebo. Therefore it has been observed that, in this murine aging model characterized by bone fragility, the irisin treatment reduced the rarefaction of trabeculae by making the whole bone segment less fragile and thus reducing the risk of fracture. Results are described in detail in Table 3a (cortical bone) and in Table 3b (trabecular bone) and depicted in FIG. 3, Panels "a" and "b".

TABLE 3a elderly osteoporotic mice - Cortical bone of tibia

| Elderly mouse | placebo-inj | Irisin-inj | P value |
|---|---|---|---|
| BMD (gr HA/cm$^3$) | 1.012 ± 0.01 | 1.02 ± 0.02* | 0.003 |
| Bone surface (mm$^2$) | 14.08 ± 0.5 | 12.7 ± 0.26 | 0.16 |
| Periosteal circumference (mm) | 12.37 ± 0.32 | 11.023 ± 0.42 | 0.07 |
| pMOI (mm$^4$) | 0.369 ± 0.03 | 0.262 ± 0.05 | 0.11 |

TABLE 3b elderly osteoporotic mice - Trabecular bone of tibia

| Elderly mouse | placebo-inj | Irisin-inj | P value |
|---|---|---|---|
| BMD (gr HA/cm$^3$) | 0.073 ± 0.009 | 0.09 ± 0.01* | 0.03 |
| BV/TV (%) | 1.96 ± 0.54 | 2.21 ± 0.17* | 0.05 |
| Trabecular thickness (μm) | 34.95 ± 0.98 | 32.86 ± 0.79 | 0.27 |
| Trabecular number (1/μm) | 0.00053 ± 0.0001 | 0.00065 ± 0.00004* | 0.04 |
| Trabecular separation (μm) | 404.69 ± 31.53 | 376.88 ± 12.86* | 0.05 |

Group 4, Osteoporotic Murine Model: Elderly "Suspended" Mouse.

15 weeks old elderly C57BL6 mice have been subjected to the absence of mechanical loading by suspension of the hind limbs, and to intraperitoneal stimulation with 100 μg/kg/week recombinant irisin for 4 weeks. The murine model of the elderly suspended mouse simulates the pathological condition of osteoporosis peculiar to aging, aggravated by an immobility condition, and is characterized by a dramatic loss of bone mass. At the end of the treatment, the tibias of suspended mice showed a loss of cortical BMD by 10% compared to that of the elderly mice maintained in control condition (normal ambulation). Data relative to controls, i.e. to elderly mice maintained in conditions of normal ambulation, are the previously described data relative to Group 3. It has been observed that the irisin treatment reduced such a loss and, in fact, in the animals treated with irisin (Irisin-inj), the cortical BMD reduction was by 5% only to the elderly suspended mice injected with placebo (placebo-inj). Regarding BMD of the trabecular bone, that in elderly suspended mice is reduced by about 45% compared to that of the elderly mice maintained in control condition (normal ambulation), the irisin treatment reduced such a loss by 15%, in fact in such animals a trabecular BMD reduction by 30% only has been observed. The drastic reduction of bone mass observed in elderly suspended mouse is also confirmed by the alterations of the other parameters of the trabecular bone. Such variations confirm the worsening of the bone fragility appearing when the immobilization is also associated with the osteoporosis in ageing caused by the decline of sex hormones. In fact, BV/TV at the level of the trabeculae of the tibias is reduced by 70% in elderly suspended mice compared to the controls, but the irisin treatment reduces such a loss by 20%, in fact in such animals (Irisin-inj) a BV/TV reduction by 50% compared to the controls has been observed. Furthermore the trabecular number, in elderly suspended mouse, is reduced by ⅓ to the control mice and the irisin treatment reduces such a loss by 20%. Results are described in detail in Table 4a (cortical bone) and in Table 4b (trabecular bone) and depicted in FIG. 4, Panels "a" and "b".

TABLE 4a elderly osteoporotic "suspended" mice - Cortical bone of tibia

| Elderly suspended mouse | placebo-inj | Irisin-inj | P value |
|---|---|---|---|
| BMD (gr HA/cm$^3$) | 0.905 ± 0.01 | 0.959 ± 0.02* | 0.02 |
| Bone surface (mm$^2$) | 13.36 ± 0.57 | 12.84 ± 0.21 | 0.4 |
| Periosteal circumference (mm) | 9.49 ± 0.12 | 8.09 ± 0.27 | 0.07 |
| pMOI (mm$^4$) | 0.353 ± 0.04 | 0.334 ± 0.02 | 0.71 |

TABLE 4b elderly osteoporotic "suspended" mice - Trabecular bone of tibia

| Elderly suspended mouse | placebo-inj | Irisin-inj | P value |
|---|---|---|---|
| BMD (gr HA/cm$^3$) | 0.039 ± 0.01 | 0.052 ± 0.004* | 0.05 |
| BV/TV (%) | 0.56 ± 0.33 | 0.95 ± 0.08* | 0.05 |
| Trabecular thickness (μm) | 32.47 ± 6.78 | 29.9 ± 2.80 | 0.7 |
| Trabecular number (1/μm) | 0.0002 ± 0.0001 | 0.00032 ± 0.0001* | 0.04 |
| Trabecular separation (μm) | 376.88 ± 8.14 | 317.38 ± 20.69* | 0.05 |

Group 5, Post-Menopausal Osteoporosis Murine Model: Young Ovariectomized Mice.

Young ovariectomized mice are the post-menopausal osteoporosis murine model commonly accepted and used by the scientific community. 6 weeks old virgin female C57BL6 mice have been divided in 2 groups: mice subjected to bilateral ovariectomy (Ovx) and mice subjected to surgery without removal of the ovaries (Sham) representing the controls. The mice of each group have been treated with irisin (100 μg/kg) or placebo starting from the day following the surgery for 4 weeks. Histomorphometric analysis of the lumbar vertebrae L3 and L4, made on sample sections included in methyl-methacrylate marked by Von Kossa/Van Gieson staining, showed that in ovariectomized mice, as expected, a reduction of bone mass has developed, as demonstrated by the analysis of the histomorphometric parameters reported in Table 5a. In particular, in such mice (Ovx placebo inj) a significant reduction of mineralized bone volume to total volume ratio (BV/TV) by 28% to the control mice (Sham placebo-inj, that is mice Sham injected with placebo), is found. In mice ovariectomized and treated with irisin (Ovx Irisin-inj) such a loss of bone mass was completely recovered. The effect was due to an increase of the trabecular thickness (Tb.Th.). In fact, as highlighted by the data reported in the table, in ovariectomized mice treated with placebo (Ovx placebo inj) the reduction of trabecular thickness was equal to 35% compared to the controls (Sham placebo-inj). Such a reduction was zeroed in ovariectomized mice treated with irisin (Ovx Irisin-inj). On the contrary, the trabecular number (Tb.N.) and trabecular separation (Tb.Sep.) were unchanged. Results are described in detail in Table 5a and depicted in FIG. 5.

TABLE 5a

Young ovariectomized mice - Trabecular bone of the lumbar vertebrae.

| Young ovariectomized | Sham | Sham | Ovx placebo- | Ovx Irisin- |
|---|---|---|---|---|
| BV/TV % | 17.899± | 17.499± | 12.913± | 17.186± |
| Trabecular number (1/mm) | 24.386 ± 0.381 | 25.772 ± 0.775 | 25.022 ± 0.016 | 23.983 ± 1.125 |
| Trabecular thickness (mm) | 0.734 ± 0.038 | 0.680 ± 0.089 | 0.477 ± 0.058*,a | 0.718 ± 0.044 *,b |
| Trabecular separation (mm) | 3.376 ± 0.058 | 3.211 ± 0.187 | 3.529 ± 0.096 | 3.468 ± 0.519 |

In Table 5a the results obtained in the histomorphometric analysis of the lumbar vertebrae in the post-menopausal osteoporosis murine model: young ovariectomized mice, are reported. Lumbar vertebrae L3 and L4 of mice (n=3 per group) subjected to bilateral ovariectomy (Ovx) or surgery without removal of the ovaries (Sham) and injected with placebo (placebo-inj) or Irisin 100 μg/kg (Irisin-inj). BD/TV, Bone Volume/Total Volume (bone volume to total volume ratio); trabecular number (Tb.N.); trabecular thickness (Tb.Th.); trabecular separation (Tb.Sep.). All values are expressed as mean±SEM.

In Table 5a 4 groups of mice have been compared, that is "Sham placebo-inj", "Sham irisin-inj", "Ovx placebo-inj" and "Ovx irisin-inj". The asterisk denotes that the value is statistically "significant" (i.e. $p<0.05$). "a" is to specify that the value is significant vs. Sham placebo-inj. "b" is to indicate that the value is significant vs. Ovx placebo-inj.

For example, in the case of BV/TV, the value is significant (reduction) in Ovx placebo-inj when compared to Sham-placebo.inj. Instead, BV/TV of Ovx Irisin-inj is significantly higher than Ovx placebo-inj. There is no significant difference between Ovx Irisin-inj and Sham placebo-inj, a demonstration of the fact that Irisin, in a mouse deprived of ovaries, brought back the bone mass (BV/TV) to a normal situation (equal to the control: Sham placebo-inj).

Figure 6A:
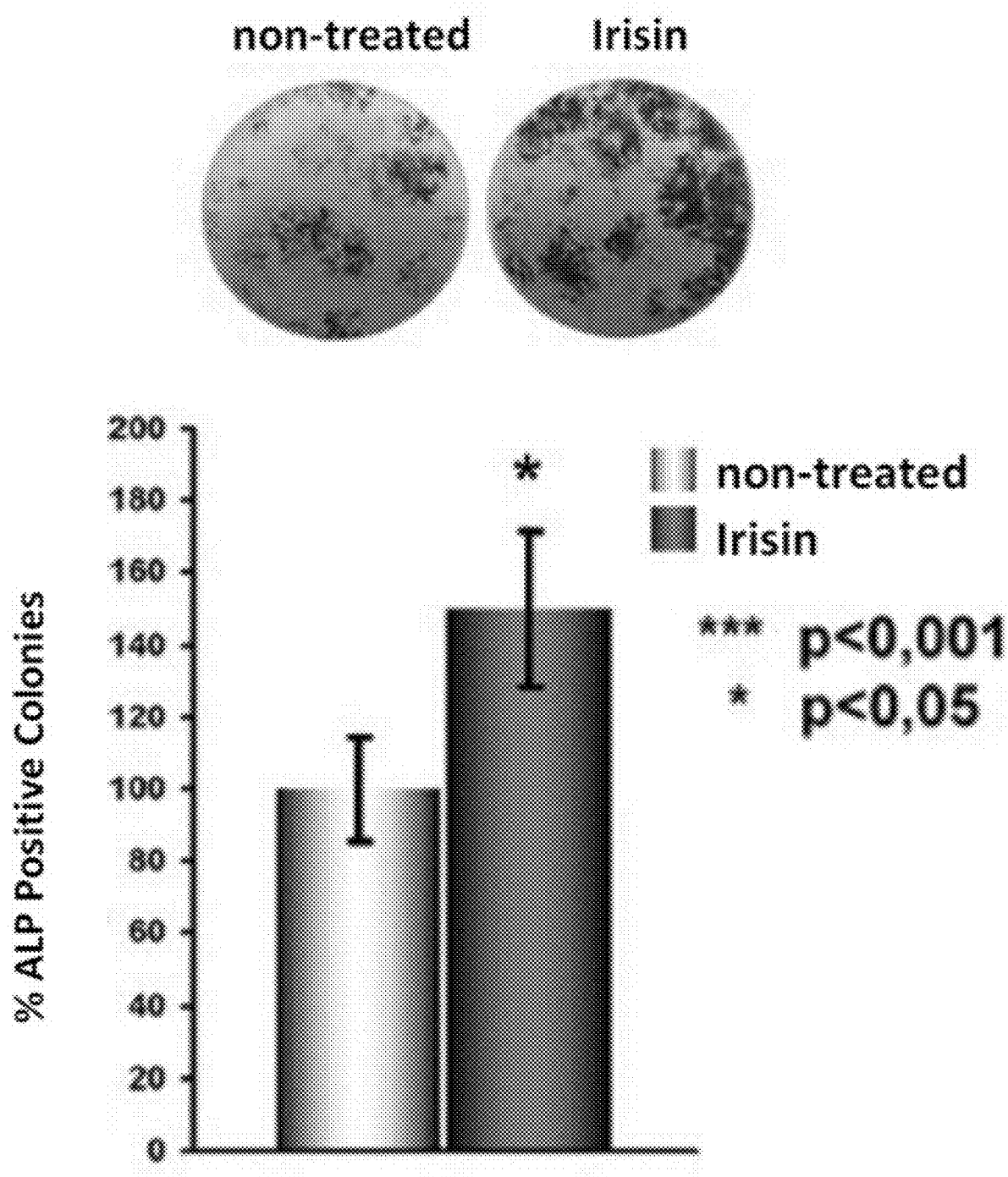
Figure 6B:
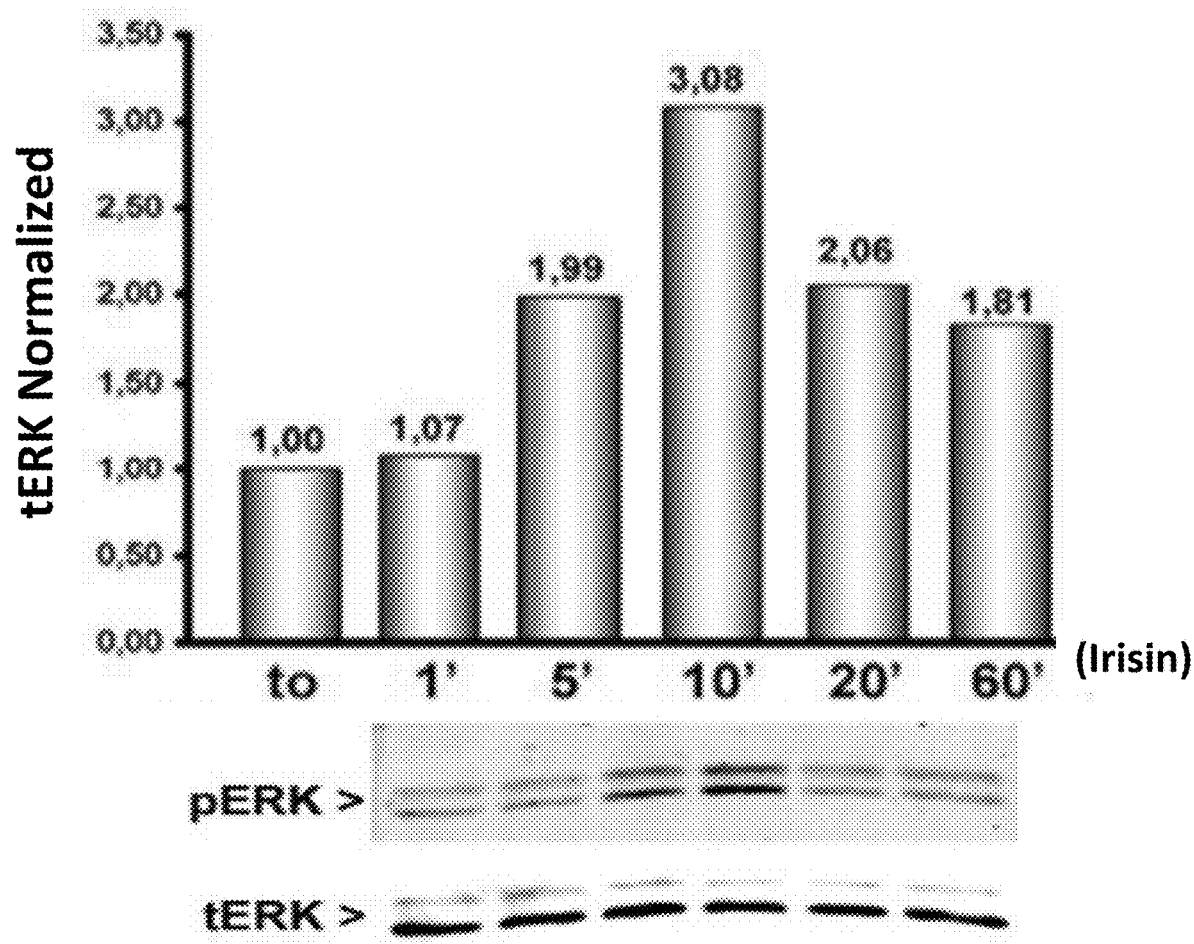
Figure 6C:
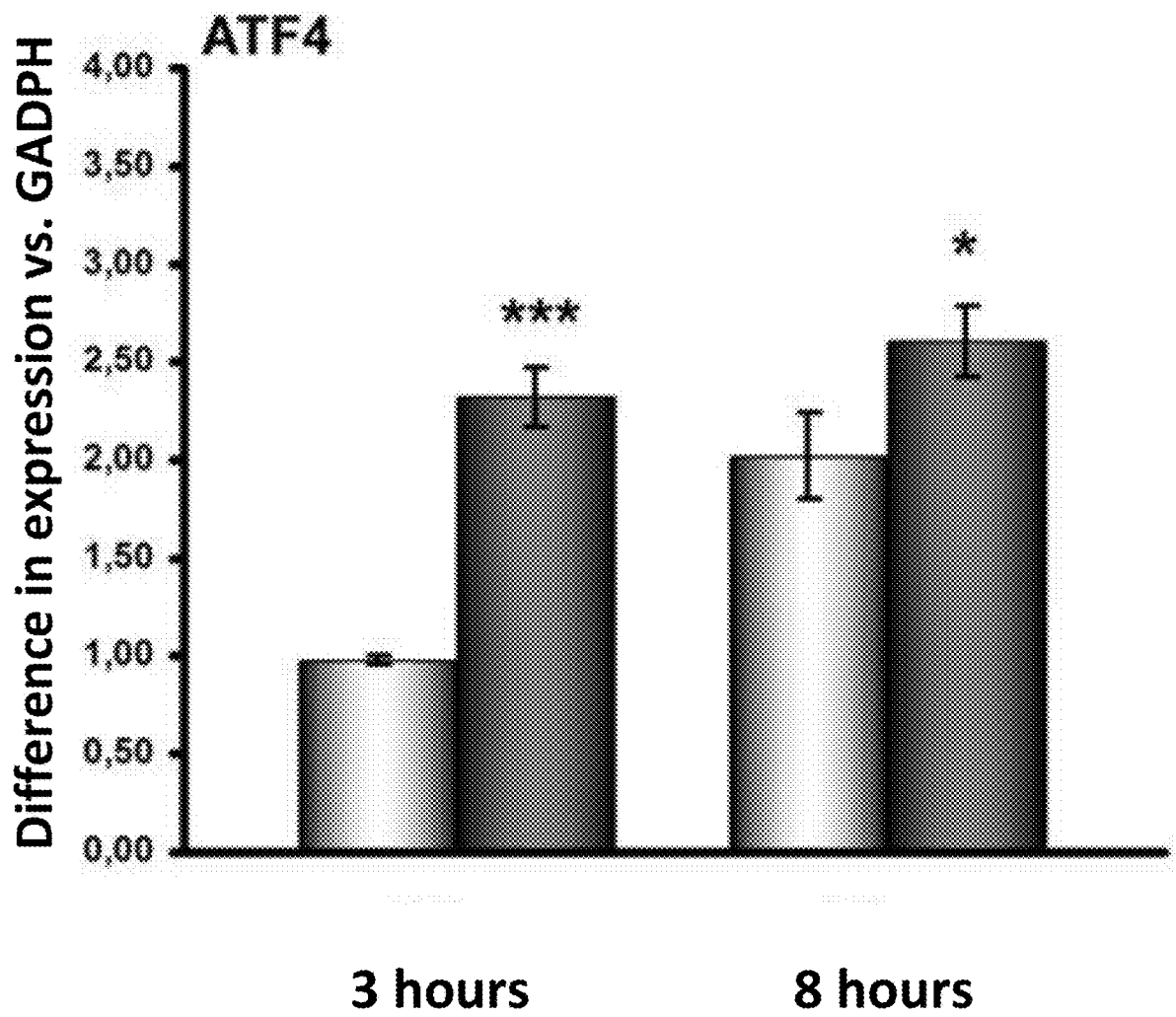
Figure 6D:
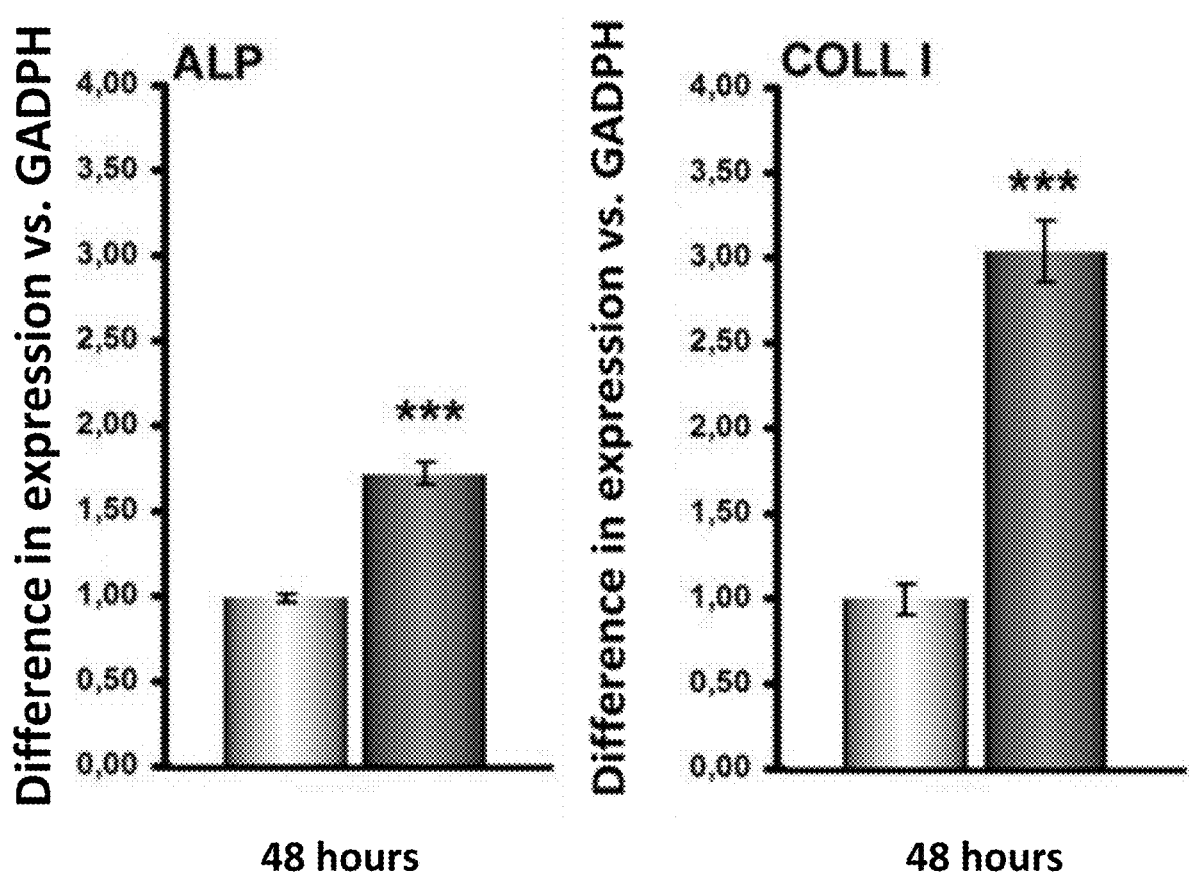

Biological Effect and Cellular Mechanisms of Irisin on Murine Osteoblasts in Vitro In order to understand the cellular mechanisms of data obtained in vivo, which have confirmed the effectiveness of irisin in the treatment of osteoporosis in different murine models, the action of this molecule has been further characterized by in vitro experiments. The results obtained confirmed that irisin exerts an anabolic effect on the bone mass. In particular, it has been hypothesized that such an effect is due to a direct action on the precursors of osteoblasts. In fact, irisin stimulates their differentiation in mature cells, as highlighted by an increased number of positive colonies for the alkaline phosphatase (ALP), i.e. the osteoblast marker (FIG. 6A). The phosphorylation of ERK MAP kinase in the osteoblasts, occurring after 5 minutes of stimulation in culture with recombinant irisin (FIG. 6B), highlights the direct action of this molecule on the bone forming cells. Furthermore, in the osteoblasts stimulated with irisin for 3 and 8 hours, an increase of the expression of the transcription factor ATF4 (FIG. 6C) occurs. The latter, being one of the transcription factors of the most abundant bone protein, the type I collagen (COLL I), induces an increase of the synthesis of this protein as well as the synthesis of ALP, as demonstrated after 48 hours treatment with irisin (FIG. 6D).

The invention claimed is:

1. A method of treating osteoporosis, said method comprising administering an effective amount of irisin with amino acid sequence (SEQ. ID NO. 1)
DSPSAPVNVTVRHLKANSAVVSWDVLEDEVVIGFAISQQKKDVRMLRFIQ

EVNTTTRSCALWDLEEDTEYIVHVQAISIQGQSPASEPVLFKTPREAEKM

ASKNKDEVTMKE to a subject in need thereof.

2. The method of treating osteoporosis as in claim 1, wherein said subject has osteoporosis.

3. The method of treating osteoporosis as in claim 1, wherein said administering comprises administering a dosage of between 500 µg/kg and 50 µg/kg of said irisin.

4. The method of treating osteoporosis as in claim 1, wherein said administering comprises administering a dosage of between 250 µg/kg and 75 µg/kg of said irisin.

5. The method of treating osteoporosis as in claim 1, wherein said administering comprises administering a dosage of 100 µg/kg of said irisin.

6. A method of treating osteoporosis, said method comprising administering a composition comprising an effective amount of irisin with amino acid sequence (SEQ. ID NO. 1)
DSPSAPVNVTVRHLKANSAVVSWDVLEDEVVIGFAISQQKKDVRMLRFIQ

EVNTTTRSCALWDLEEDTEYIVHVQAISIQGQSPASEPVLFKTPREAEKM

ASKNKDEVTMKE to a subject in need thereof.

7. The method of treating osteoporosis as in claim 6, wherein said composition further comprises excipients and/or additives for pharmaceutical use.

* * * * *

SEQUENCE LISTING

```
<160> NUMBER OF SEQ ID NOS: 1

<210> SEQ ID NO 1
<211> LENGTH: 112
<212> TYPE: PRT
<213> ORGANISM: Artificial Sequence
<220> FEATURE:
<223> OTHER INFORMATION: Recombinant Irisin

<400> SEQUENCE: 1

Asp Ser Pro Ser Ala Pro Val Asn Val Thr Val Arg His Leu Lys Ala
1               5                  10                  15

Asn Ser Ala Val Val Ser Trp Asp Val Leu Glu Asp Glu Val Val Ile
            20                  25                  30

Gly Phe Ala Ile Ser Gln Gln Lys Lys Asp Val Arg Met Leu Arg Phe
        35                  40                  45

Ile Gln Glu Val Asn Thr Thr Thr Arg Ser Cys Ala Leu Trp Asp Leu
    50                  55                  60

Glu Glu Asp Thr Glu Tyr Ile Val His Val Gln Ala Ile Ser Ile Gln
65                  70                  75                  80

Gly Gln Ser Pro Ala Ser Glu Pro Val Leu Phe Lys Thr Pro Arg Glu
                85                  90                  95
```

```
Ala Glu Lys Met Ala Ser Lys Asn Lys Asp Glu Val Thr Met Lys Glu
            100                 105                 110
```